(12) United States Patent
Brass et al.

(10) Patent No.: US 11,185,433 B2
(45) Date of Patent: Nov. 30, 2021

(54) HALLUX VALGUS SANDAL HAVING AT LEAST ONE GREAT TOE STRAP SECTION AND ONE HOLDING STRAP SECTION

(71) Applicant: Hallufix AG, Grünwald (DE)

(72) Inventors: Manfred Brass, Grünwald (DE); Franz Fischer, Amberg (DE)

(73) Assignee: Hallufix AG, Grünwald (DE)

( * ) Notice: Subject to any disclaimer, the term of this patent is extended or adjusted under 35 U.S.C. 154(b) by 0 days.

(21) Appl. No.: 16/767,376

(22) PCT Filed: Nov. 27, 2018

(86) PCT No.: PCT/EP2018/082679
§ 371 (c)(1),
(2) Date: May 27, 2020

(87) PCT Pub. No.: WO2019/102033
PCT Pub. Date: May 31, 2019

(65) Prior Publication Data
US 2020/0383813 A1    Dec. 10, 2020

(30) Foreign Application Priority Data

Nov. 27, 2017  (DE) ..................... 20 2017 107 165.0
Jan. 24, 2018  (DE) ..................... 10 2018 201 113.3

(51) Int. Cl.
*A43B 7/26* (2006.01)
*A61F 5/01* (2006.01)
(Continued)

(52) U.S. Cl.
CPC .............. *A61F 5/019* (2013.01); *A43B 3/105* (2013.01); *A43B 3/126* (2013.01); *A43B 7/1445* (2013.01); *A43B 7/26* (2013.01)

(58) Field of Classification Search
CPC ......... A61F 5/019; A43B 3/126; A43B 3/122; A43B 3/12; A43B 3/103; A43B 3/105; A43B 3/10; A43B 3/102; A43B 7/26
(Continued)

(56) References Cited

U.S. PATENT DOCUMENTS 3,066,678 A    12/1962  Riecken
3,275,002 A     9/1966  Scholl
4,632,103 A *  12/1986  Fabricant .............. A61F 5/019
                                                          602/30
(Continued)

FOREIGN PATENT DOCUMENTS

DE          855612 C    11/1952
DE         1261778 B     2/1968
WO      2013160377 A1   10/2013

OTHER PUBLICATIONS

International Search Report for priority application PCT/EP2018/082679, 5 pages, dated Mar. 21, 2019.

*Primary Examiner* — Marie D Bays
(74) *Attorney, Agent, or Firm* — Ohlandt, Greeley, Ruggiero & Perle, LLP

(57) ABSTRACT

A hallux valgus sandal for treating at least great toe malpositions, having a sole element with an outsole and a footbed, with a great toe strap section for the lateral positional fixing of the great toe and with a holding strap section, which holds the sandal on the foot when the sandal is worn. The wrap length of the great toe strap section can be changed in such a way that an adjustable corrective force can be exerted on the great toe. A metatarsus strap section is also provided, the wrap length of which can be changed, wherein both strap sections can be coupled to each other such that a metatarsus corrective force acting laterally on the metatarsal bone can be varied to press the metatarsal bone on the foot inner side in the lateral direction towards the foot outer side. As a result of said metatarsus corrective force, a hallux corrective force in the direction toward the foot inner side can be exerted, (Continued)

wherein the great toe strap section is guided backwards from the great toe at an angle and enters a channel on the inside of the sole element that is arranged in the metatarsus region of the sandal.

14 Claims, 9 Drawing Sheets

(51) Int. Cl.
*A43B 3/12* (2006.01)
*A43B 7/14* (2006.01)
*A43B 3/10* (2006.01)

(58) Field of Classification Search
USPC .......................................................... 36/11.5
See application file for complete search history.

(56) References Cited

U.S. PATENT DOCUMENTS

| | | | |
|---|---|---|---|
| 4,813,162 A * | 3/1989 | Harris | A43B 3/108 |
| | | | 36/11.5 |
| 6,202,325 B1 * | 3/2001 | Kim | A43B 3/105 |
| | | | 36/11.5 |
| 2007/0074334 A1 * | 4/2007 | Steel | A43B 3/105 |
| | | | 2/239 |
| 2011/0061262 A1 * | 3/2011 | Krauss | A61F 5/019 |
| | | | 36/11.5 |
| 2011/0130695 A1 | 6/2011 | Rafique | |
| 2011/0179674 A1 | 7/2011 | Heid | |
| 2014/0123440 A1 | 5/2014 | Capra et al. | |
| 2015/0101213 A1 | 4/2015 | Brass | |
| 2016/0242508 A1 | 8/2016 | Heid | |
| 2019/0350304 A1 * | 11/2019 | Velazquez | A43B 5/00 |
| 2020/0229531 A1 * | 7/2020 | Driscoll | A43B 3/128 |

* cited by examiner

HALLUX VALGUS SANDAL HAVING AT LEAST ONE GREAT TOE STRAP SECTION AND ONE HOLDING STRAP SECTION

CROSS-REFERENCE TO RELATED APPLICATIONS

The present application is a National Stage application of PCT Application No. PCT/EP2018/082679 and is claiming priority of German Patent Application No. 20 2017 107 165, filed on Nov. 27, 2017 and German Patent Application No. 10 2018 201 113, filed on Jan. 24, 2018 the entirety of each of which is incorporated by reference herein.

TECHNICAL FIELD

A hallux valgus sandal is provided with a great toe strap section and a holding strap section, and preferably with a sole element having an outsole and a footbed, a great toe strap section for laterally fixing position of the great toe and a metatarsus strap section which, in a state in which the sandal is worn, circularly encloses the metatarsal bones of a foot hold on the sole element and which is adjustable in its wrap or enclosing length.

Technological Background

From the prior art, hallux valgus sandals are known. US Pat. Pub. 2016/0242508 A1 discloses a therapeutic hallux valgus sandal for treating malpositions at least of great toes, comprising a sole element having an outsole and a footbed attached to a foot in a state in which the sandal is worn at the foot, a holding strap section fixed to the sole element and configured for holding the sandal at the foot, and a great toe strap section. The great toe strap section has a first end region which is fixed to or embedded in the sole element in a region of the sole element arranged between the great toe and the adjacent toe and is variably adjustable in its wrap length around the great toe such that an adjustable corrective force is exertable on the great toe. Upon adjusting the great toe strap section, also the holding strap section arranged in the metatarsus region of the foot is adjusted since both adjustment straps are coupled to one another. Similar configurations of therapeutic sandals are disclosed in U.S. Pat. Nos. 3,066,678 and 3,275,002.

The sandals according to the prior art have the disadvantage that the great toe strap section fits closely to and is guided across the great toe. This allows only small adjustments since a force application point is unfavorably positioned which results in a low torque acting upon the toe around the metatarsophalangeal joint of the great toe. Upon tightening the great toe strap, a rotation of the great toe around its longitudinal axis is inevitably effected, which is particularly disadvantageous. Further, the size of the great toe strap section in the region of the great toe, in particular at its entry position into the sole region of the sandal, limits the possible lateral shifting range of the great toe. The clinical picture of hallux valgus comprises both axial displacement and rotation of the great toe. In fact, the sandals known from the prior art even contribute to the both negative aspects.

WO 2013/160377 A1 discloses a hallux valgus sandal, comprising a sole element with an outsole and a footbed. The sandal further comprises a great toe support for laterally supporting the great toe and a metatarsal strap which, together with the sole element, circularly encloses the metatarsal bones in a state in which the sandal is worn and which is variably adjustable in its length. A pressure pad is provided at the inside of the sandal in the region of the metatarsus which, upon applying the metatarsal strap to the pressure pad, exerts a laterally directed force onto the inner metatarsal bone. The metatarsal strap is divided into two parts such that the circular length of the metatarsal strap is adjustable by the degree of overlap between the two parts of the metatarsal strap. By virtue of the force exerted onto the metatarsal bone at the foot inner side by the pressure pad, which pushes the metatarsal bone outwardly, the great toe is subjected to an increased alignment directed inwardly. However, the great toe strap is fixed and not adjustable and merely serves for laterally supporting the great toe. Thus, the corrective action of the alignment of the great toe is performed in an indirect manner by means of the great toe correction effected by the pressure pad. However, an additional therapeutic unit for directly correcting the malposition of the great toe is not provided It is an object of the present disclosure to provide a hallux valgus sandal in which each one of a great toe strap section and a metatarsal strap section enables to therapeutically affect the alignment of a great toe and metatarsal bones.

This object is solved by a hallux valgus sandal having the technical features described herein.

According to the present disclosure, the hallux valgus sandal for treating malpositions of at least great toes comprises a sole element having an outsole and a footbed attached to a foot when being worn at the foot, a holding strap section which is fixed to the sole element and configured for holding the sandal at the foot, and a great toe strap section. The holding strap section is configured for holding the sandal at the foot in a region near to the great toe strap section. For doing so, the holding strap section may be arranged in the region of the toes, specifically in addition to the great toe strap section which is designed and provided such that it enables to correct, i.e. by way of a therapeutic effect, a malfunction of the great toe. In the context of hallux valgus, according to which the great toe has a malposition towards a foot outer side, i.e. in direction to the other toes, the term correction means that the malposition is to be corrected to such an extent that the great toe is realigned substantially in direction of the foot.

When therapeutically treating such a malposition of the great toe, provided that the treatment is successful, the great toe is repositioned into its original alignment, i.e. in direction of the foot, during the course of the treatment. Therefore, the required corrective force varies during the treatment to correct the great toe's position by realigning it from its outwardly oriented malposition to a straight position. For doing this in a corrective manner according to the therapeutic success, the great toe strap section has a first end region, which is fixed to or embedded in the sole element. Preferably, the great toe strap section is configured such that a force is exerted to its end which is arranged opposed to its fixation to the sole element. The force ensures that the wrap length of the great toe strap section around the great toe is adjustable such that an adjustable corrective force is exertable on the great toe. For doing so, the second end, which is opposed to the fixation to the sole element, is varied in its position, preferably pulled, to decrease the wrap length such that the corresponding corrective force is exertable onto the great toe. Thus, it is possible, to achieve a therapeutic effect on the malposition of the great toe exclusively by means of a great toe strap section, which is adjustable in its wrap length around the great toe. This means that the corrective force acting on the great toe for correcting its malposition is adaptable to the respective therapeutic effect which has already been achieved. It is not necessary that the additionally provided holding strap section effects a therapeutic effect by itself. Rather, it primarily serves to hold the hallux valgus sandal at the foot.

In an embodiment, the great toe strap section is guided obliquely backwards from the first end region over the region of the great toe and, at an inner side of the hallux valgus sandal, enters a channel in the sole element which leads to an outside of the hallux valgus sandal, wherein the channel is arranged in the metatarsus region of the hallux valgus sandal.

This guiding of the great toe strap section prevents the great toe from being twisted around its longitudinal axis upon tightening the great toe strap. Further, the oblique pathway causes a shift of the force application point at the great toe and thus an extension of the lever compared to configurations known from the prior art. By guiding the great toe strap section behind the metatarsophalangeal joint into a channel in the sole element which is arranged in the metatarsus region of the foot, the sole element is only minimally weakened. In particular, no weakening occurs in the region of the metatarsophalangeal joint at which the pressure on the sole element is particularly high. By such a configuration according to the present disclosure, in contrast to the sandals known from the prior art, a shift of the axis and a rotation of the great toe around its longitudinal axis is prevented.

In an embodiment, a metatarsus strap section is provided in addition to the great toe strap section which is adjustable in its wrap length. The metatarsus strap section is fixed to or embedded in the sole element at its respective end regions and the wrap length around the metatarsus region is variably adjustable such that an adjustable corrective force is exertable on the metatarsus region. Since the wrap length of the metatarsus strap section is preferably adjustable, a corresponding corrective force may be exertable on the metatarsal bone or the metatarsal bones such that the corrective force for correcting the metatarsal bones in their malposition according to the anatomical conditions can provide a therapeutic effect on the hallux valgus. Thus, in addition to the great toe strap section being adjustable in its wrap length, the metatarsus strap section may provide a therapeutic effect.

The advantage of such a device is that the wrap length of the great toe strap section and the wrap length of the metatarsus strap section can be used separately for exercising a corrective force in order to achieve a therapeutic effect on malpositions of toes and/or metatarsals. This is because both strap sections are configured to be adjustable in their wrap length independently from one another.

Preferably, the hallux valgus sandal has a sole element with an outsole and a footbed, a great toe strap section for laterally fixing the position of the great toe, and a metatarsus strap section which, in a state in which the sandal is worn, circularly encloses the metatarsal bones of a foot hold on the sole element and which is adjustable in its wrap length. Upon adjusting the wrap length of the metatarsus strap section, for example, by shortening the wrap length of the metatarsus strap section, the corrective force increases in a direction towards the foot outer side which, already for anatomical reasons, may have a positive effect on the alignment of the great toe by correcting the great toe's position from the malposition directed towards a foot outer side to a correct position directed towards the foot inner side. The metatarsus strap section and the great toe strap section may be coupled to one another such that, when the metatarsus strap section is actuated, i.e. by adjusting its wrap length, also the great toe strap section is actuated by being tightened or loosened. In this way, upon tightening or loosening the metatarsus strap section, the great toe strap section may exert a stronger or weaker corrective force in direction of the foot inner side. The coupling between the metatarsus strap section and the great toe strap section may be provided inside the outsole or between the footbed and the outsole in case the actual footbed is provided in an insole being detachable from the sandal. The part of the metatarsus strap section being arranged in the inside of the outsole is preferably diagonally connected to the great toe strap section in the inside of the sandal and is guided out of the outsole or from between the footbed and the outsole such that it forms a strap. The thus formed strap is intended and suitable for lateral fixation of the great toe. Further, by means of the strap, the great toe corrective force may be adjustably exertable in direction of the foot inner side. The material of the metatarsus strap section and the material of the great toe strap section may be substantially tension-resistant such that the parts of the strap sections at the metatarsus region as well as at the great toe region may exert their previously described corrective force, respectively.

In this way, it is not only possible to omit a pressure pad described in the prior art and being mandatory in the known configurations. Further, the sandal according to the disclosure may be put more easily into a fashionable shape, without negatively affecting the therapeutic effect of the sandal.

According to a first exemplary configuration, the metatarsus strap section may be divided and may comprise a foot inner side part and a foot outer side part, wherein the foot inner side part of the metatarsus strap section may be coupled to the great toe strap section and may be arranged in the inside of the outsole. This means that the metatarsus strap section may laterally enter into the outsole, may be guided within and through the metatarsus sole, and may come out in the region of the great toe so as to form the strap of the great toe strap section for lateral fixation. Preferably, the metatarsus strap section enters into the sole section by laterally entering into a channel such that the metatarsus strap section covers the great toe strap section at an entry region of the outsole or such that the great toe strap section covers the metatarsus strap section at an entry region of the outsole.

The wrap length of the metatarsus strap section may preferably be shortened by pulling the foot inner side part of the metatarsal strap section over its foot outer side part, thereby, for example, increasing the corrective force and allowing the metatarsus strap section and therefore also the great toe strap section for being adjustable according to the therapeutic correction.

According to another exemplary configuration, it may also be possible to shorten the wrap length by folding the metatarsus strap section. At the metatarsus strap section, which may be designed in a substantially closed manner, a unit may be provided, by means of which an unfolding of the metatarsus strap section over an underlying area and its fixation is achieved in an unfolded manner such that the length of the metatarsus strap section is also shortened.

Preferably, the footbed, at its side facing the foot inner side, is provided with a raised edge in the region of the metatarsus strap section which, upon decreasing the wrap length of the metatarsus strap section either by pulling over a divided metatarsus strap section or by unfolding or folding a closed metatarsus strap section, exerts the corrective force on the metatarsal bone in the manner of a pressure pad.

However, a pressure pad as such is not required. Due to the design of the footbed, the effect of a pressure pad may be achieved.

According to a further development, it may also be possible that metatarsus strap section, in the region of its foot inner side, has a pad or baled cushion provided in the form of a pressure pad which, upon decreasing the wrap length of the metatarsus strap section, additionally increases the corrective force exerted on the metatarsal bone. Preferably, the pad or baled cushion is detachable and re-attachable by means of a suitable detachable connection such that the size of the pad and thus the additionally exerted corrective force is adjustable depending on the therapeutic success.

According to an exemplary configuration, a rotary knob may be arranged at the metatarsus strap section for shortening its wrap length. The rotary knob interacts with a tension element, such as a rope, cable, wire, etc., the both ends of which are attached to the metatarsus strap section in the region of its fixation to the foot outer side of the outsole. Upon turning the rotary knob, the rope may be wound onto a winding section, such as a cylinder, thereby shortening the effective wrap length of the metatarsus strap section. By turning the rotary knob, the wrap length of the metatarsus strap section may be increased or decreased depending on the therapeutic success of the treatment. For example, the shortening of the wrap length may be performed or adjusted by the patient, if, for example, the patient finds out that, at the beginning of the treatment with the sandal, the exerted corrective force is too high and may causes pain.

The coupling of the metatarsus strap section and the great toe strap section may be provided by integrally connecting the metatarsus strap section to the great toe strap section and by guiding the metatarsus strap section thorough the inside of the sole element such that, by varying the overlap of the foot inner side part and the foot outer side part of the metatarsus strap section, the great toe strap section is simultaneously tightened so as to enable to increase a corrective force exerted on the great toe. Upon increasing the wrap length of the metatarsus strap section, the corrective force exerted on the great toe may accordingly be decreased.

According to a second exemplary configuration, a tensioning unit provided in the form of a rotary knob may be arranged at the foot inner side part of the metatarsal strap element and may be connected to a tension element provided in the form of a rope, cable, wire or the like, wherein the tensioning element is guided through the inside of the sole element up to an end of the great toe strap section arranged inside the sole element, and wherein the end of the great toe strap section is opposed to the fixation point of the great toe strap section. In this way, a connection, but not an integral connection between the strap sections of the great toe and the metatarsus region is to be achieved. The coupling is thus provided via the tension element. Therefore, upon shortening the tension element by winding it up with the rotary knob, both the wrap length of the metatarsus strap section as well as the wrap length of the great toe strap section may be varied. The coupling between the metatarsus strap section and the great toe strap section has the advantage that, by means of a single adjustment unit, the corrective force required for the desired therapeutic effect and provided in both the metatarsus region and the great toe region and can be adjusted by a single actuation. In the context of the present disclosure, the term tension element refers to an element which is designed and suitable to be subjected to tensile stresses and which is provided with an inherent rigidity so as to be capable of exerting a pushing force onto the respective strap section when the wrap length is increased.

The strap sections are preferably flexible and tension-resistant and are preferably made of a textile material or of a multilayer composite material.

Only one tensioning unit for the great toe strap section may be provided for adjusting the corrective force acting on the great toe or, in addition, a second tensioning unit may be provided, optionally in the form of a rotary knob, which may be implemented such that the corrective force acting on the metatarsus region is adjustable upon adjusting the wrap length of the metatarsus strap section. The main advantage may be that the corrective forces respectively exerted on the great toe region and the metatarsus region are individually adjustable and thus independently adjustable from one another. For doing so, two tensioning units may be required in order to adjust the therapeutic corrective force applied in the two regions. However, an advantage may be the independence of adjusting the different regions.

In the configuration according to the first aspect of the present disclosure, the holding strap section present, for example, in the region of the toes may be replaced by a strap section in the form of the metatarsus strap section, the wrap length of which is variably adjustable according to the disclosure. In this case, a holding section in the area of the toes would thus not be required. However, it is also possible that the holding strap section is constituted by the metatarsus strap section as described above, but yet additional strap sections which are not intended for providing a therapeutic effect
may be arranged in the region of the toes.

Preferably, the metatarsus strap section is provided in the form of a divided section comprising a foot inner side part and a foot outer side part, wherein these parts preferably have a certain degree of overlapping or coverage relative to one another. By varying or changing the overlap or coverage of the two ends of the two parts of the metatarsus strap section, the wrap length of the metatarsus strap section may be adjusted. Preferably, this may be performed correspondingly by means of an appropriately designed tensioning unit if, at a first part of the metatarsus strap section, the tension element is connected to the rotary knob or the winding cylinder arranged thereon and the ends of the tension element are connected to another part of the metatarsus strap section.

According to a further development, the wrap length of the metatarsus strap section may be adjusted upon folding or unfolding this section.

If, according to a further development, the coupling of the great toe strap section and the metatarsus strap section is provided by an integral or one-piece connection between, for example, the foot outer side part of the metatarsus strap section and the great toe strap section, only one tensioning unit may be required for adjusting the wrap length of both the metatarsus strap section and the great toe strap section.

The rotary knob, which forms an substantial part of the tensioning unit, is preferably designed such that it comprises a winding section on which the tension element is windable to be shorten, wherein an unwinding action may be performed for lengthening the tension element. Further, the rotary knob is designed such that it is lockable in a respectively set winding position associated to a predefined wrap length. The locking action of the rotary knob may have the advantage that, in a state in which the hallux valgus sandal is worn, unintended loosening is prevented and thus deterioration of the therapeutic effect of the corrective force induced by the reduction of the wrap length. Instead of the rotary knob, a clamping device may be provided for fixing or locking the tension element in a desired position.

Further advantages, embodiments and details of the disclosure will be more readily appreciated by reference to the following detailed description of embodiments when being considered in connection with the accompanying drawings in which.

Figure 6:
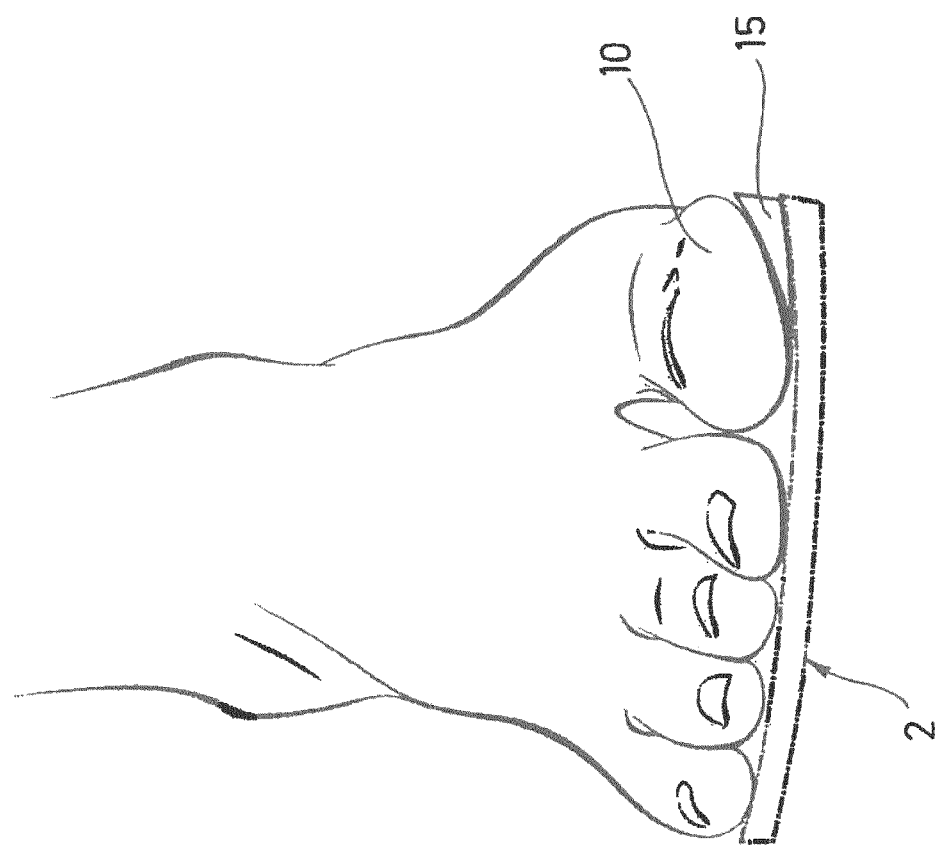
Figure 7:
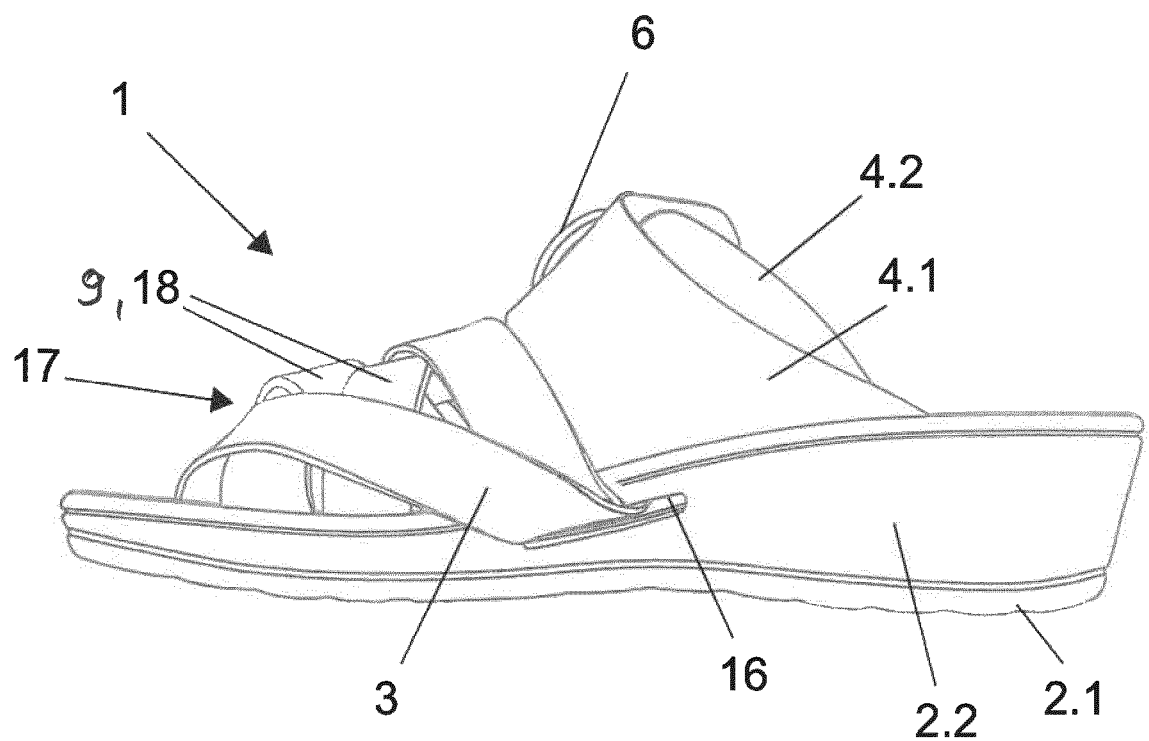
Figure 8:
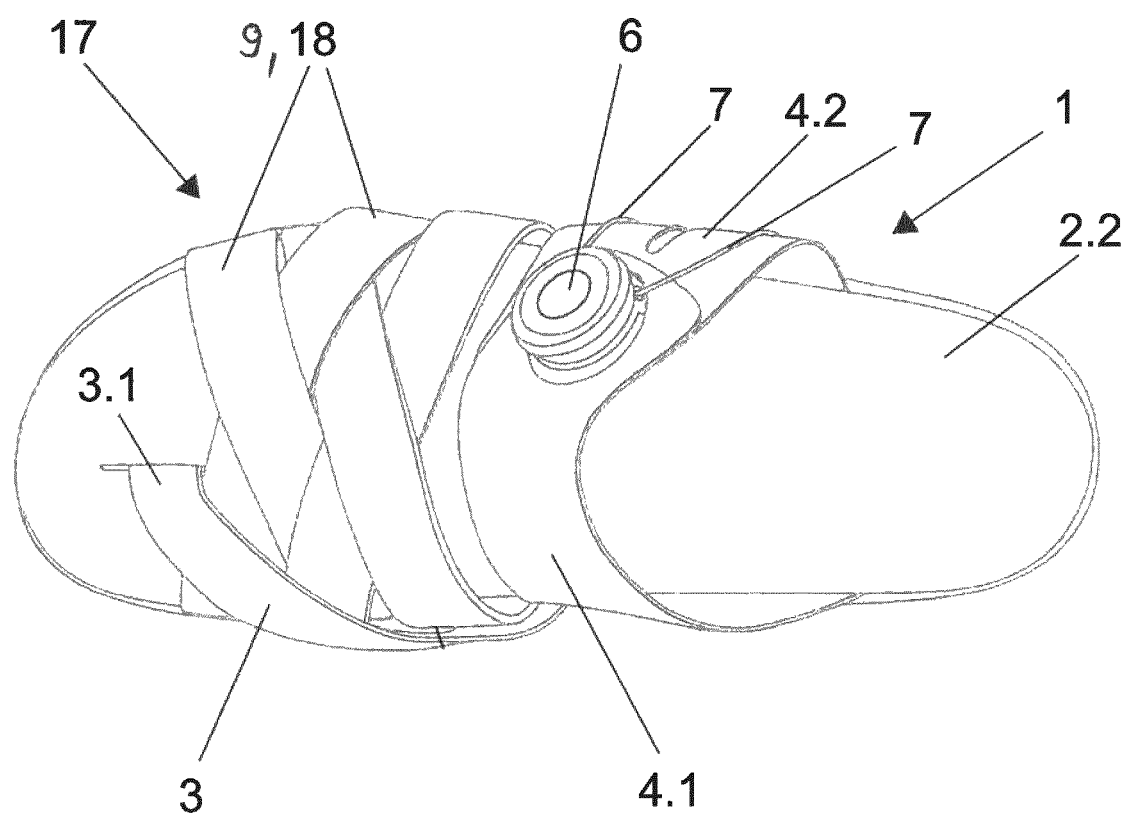
Figure 9:
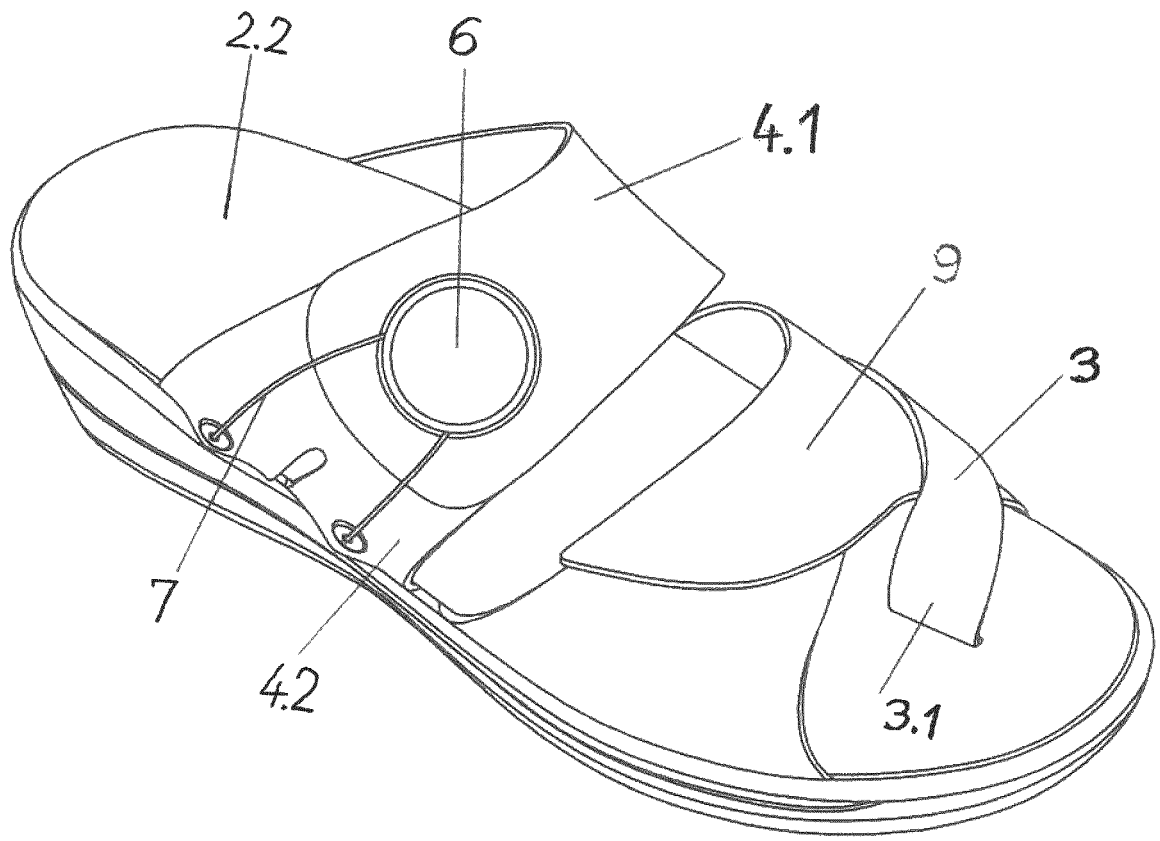

FIG. 6 schematically shows a general view of a foot arranged on the sole element according to another embodiment, without showing the strap sections;

FIG. 7 shows a perspective view as a side view of the foot inner side according to another embodiment;

FIG. 8 shows a perspective view as a top view of the embodiment depicted in FIG. 7; and FIG. 9 shows a perspective top view of another embodiment.

Figure 1:
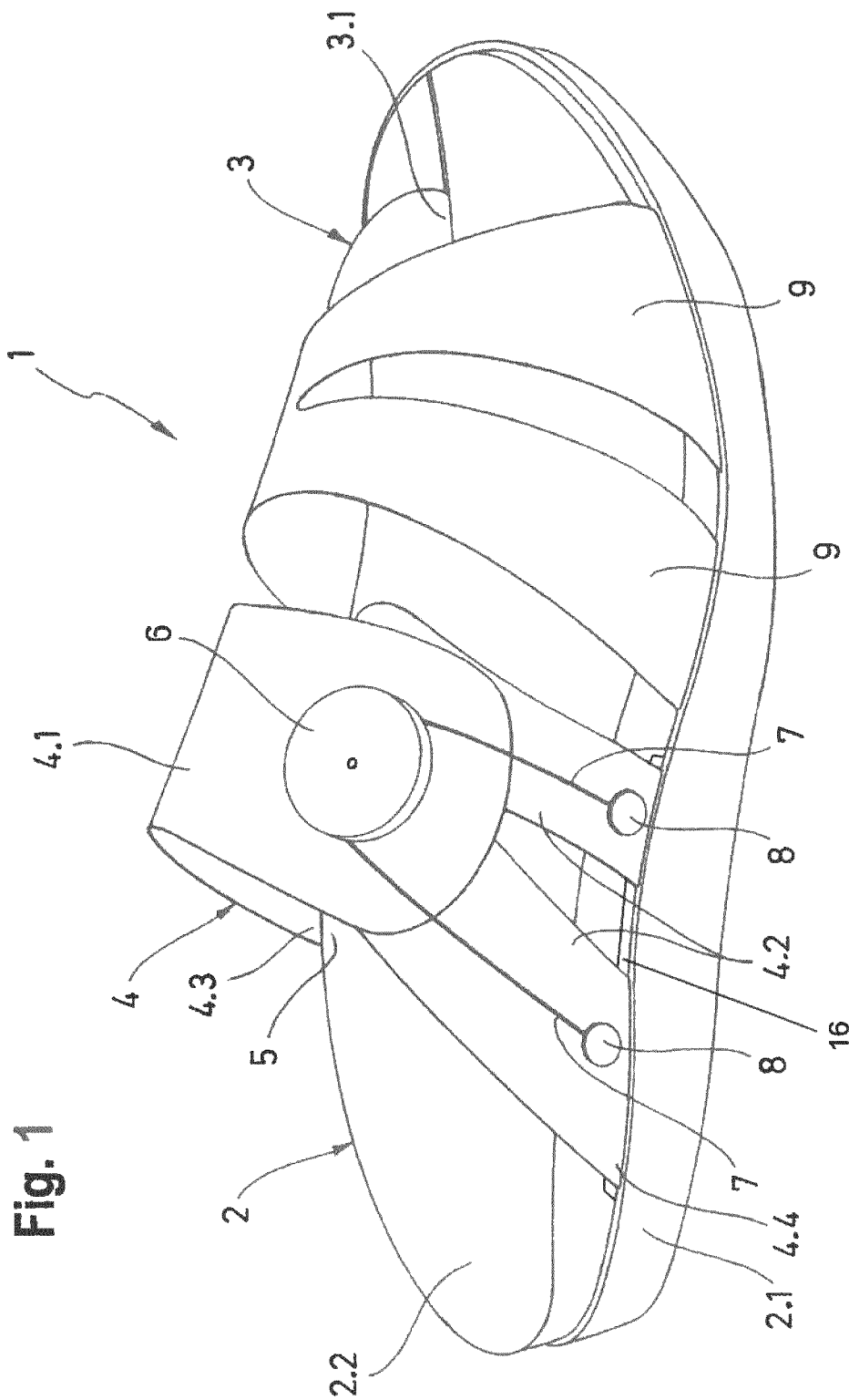
FIG. 1 shows a perspective top view of a sandal according to the disclosure from an oblique angel from above.

FIG. 1 shows a perspective view of a sandal according to the disclosure from an oblique angel from above the foot outer side. The hallux valgus sandal 1 comprises a sole element 2 having a known two-part design which consists of an actual outsole 2.1 and a footbed 2.2, wherein the footbed is provided in an insole which is arranged on the outsole 2.1 in the inside of the sandal 1. The footbed 2.2 may be attached, particularly glued, to the outsole 2.1.

The sandal 1 has a basic design comprising a great toe strap section 3 and a metatarsus strap section 4. The metatarsus strap section 4 is divided and comprises a foot inner side part 4.1 and a foot outer side part 4.2. The foot inner side part 4.1 is arranged on the foot outer side part 4.2 in an overlapping manner, i.e. the foot inner side part 4.1 overlaps the foot outer side part 4.2. In between the great toe strap section 3 and the metatarsus strap section 4, two intermediate strap sections 9 are provided which emphasize the sandal-like character of the therapeutic shoe, which however do not affect the therapeutic success for treating hallux valgus. If, for example, the metatarsus strap section 4 is not present or missing, the intermediate strap sections serve as holding strap sections. The metatarsus strap section 4 with its enclosing arrangement around the metatarsus region can be set and is adjustable in its wrap length. Thus, the wrap length is defined by the two overlapping parts 4.1 and 4.2 of the metatarsus strap section 4 and the footbed in the insole below a foot arranged in the sandal. By means of a rotary knob 6 which interacts with attachments 8 via a tension element connection in the form of a rope, wherein the rotary knob is arranged on the foot inner side part 4.1 and the attachments 8 are arranged at the foot outer side part 4.2 of the sandal, the length of the rope is decreased or increased upon actuation of the rotary knob, in fact depending on the direction of rotation of the rotary knob. In this way, the length of the overlap of the foot inner side part 4.1 on the foot outer side part 4.2 is decreased or increased, accordingly, such that, upon decreasing the length of the tension element 7, the wrap length of the metatarsus strap section 4 enclosing the metatarsus region decreases.

The foot outer side part 4.2 of the metatarsus strap section 4 is connected to the great toe strap section 3 in the inside of the sandal 1, i.e. as shown in FIG. 1, either in a region between the insole comprising the footbed and the actual outsole or underneath the insole in case the actual outsole and the footbed are integrally provided. That is, the foot outer side part 4.2 of the metatarsus strap section 4 is guided in a channel 16 within the sandal 1 from the outer side of the sandal, into which the foot outer side part 4.2 of the metatarsus strap section 4 enters, to its opposing side, i.e. the foot outer side part 4.2 comes out from the sole element at the foot inner side. Therefore, the second end region 3.2 of the thus formed great toe strap section is also provided on the foot inner side. The end region 4.4 of this part of the metatarsus strap section 4 and the great toe strap section 3, i.e. the end located at the great toe strap section, is attached to the actual outsole 2.1 of the sandal 1. In this region, the first end region 3.1 of the great toe strap section 3 is fixed to the outsole 2.2, while its second end region 3.2 merges into foot outer side part 4.2 of the metatarsus strap section 4 in channel 16 within the sole element 2. For assembly reasons, the end of the great toe strap section 3 is fixed to the actual outsole 2.1 such that the actual strap of the great toe strap section 3 is provided at the foot inner side of the sandal 1.

The footbed 2.2 is provided with a raised edge at its foot arch in direction to the foot inner side, wherein the raised edge 5 contributes to an increased corrective force applied to the metatarsal bones upon shortening the wrap length of the metatarsus strap section 4. However, it is also possible that a separate pad is provided instead of the raised edge 5, wherein the same functionality of applying the corrective force on the metatarsal bones is allocated to the pad so as to provide a supportive correction of the malposition of the great toe upon shortening the wrap length of the metatarsus strap section 4.

Figure 2:
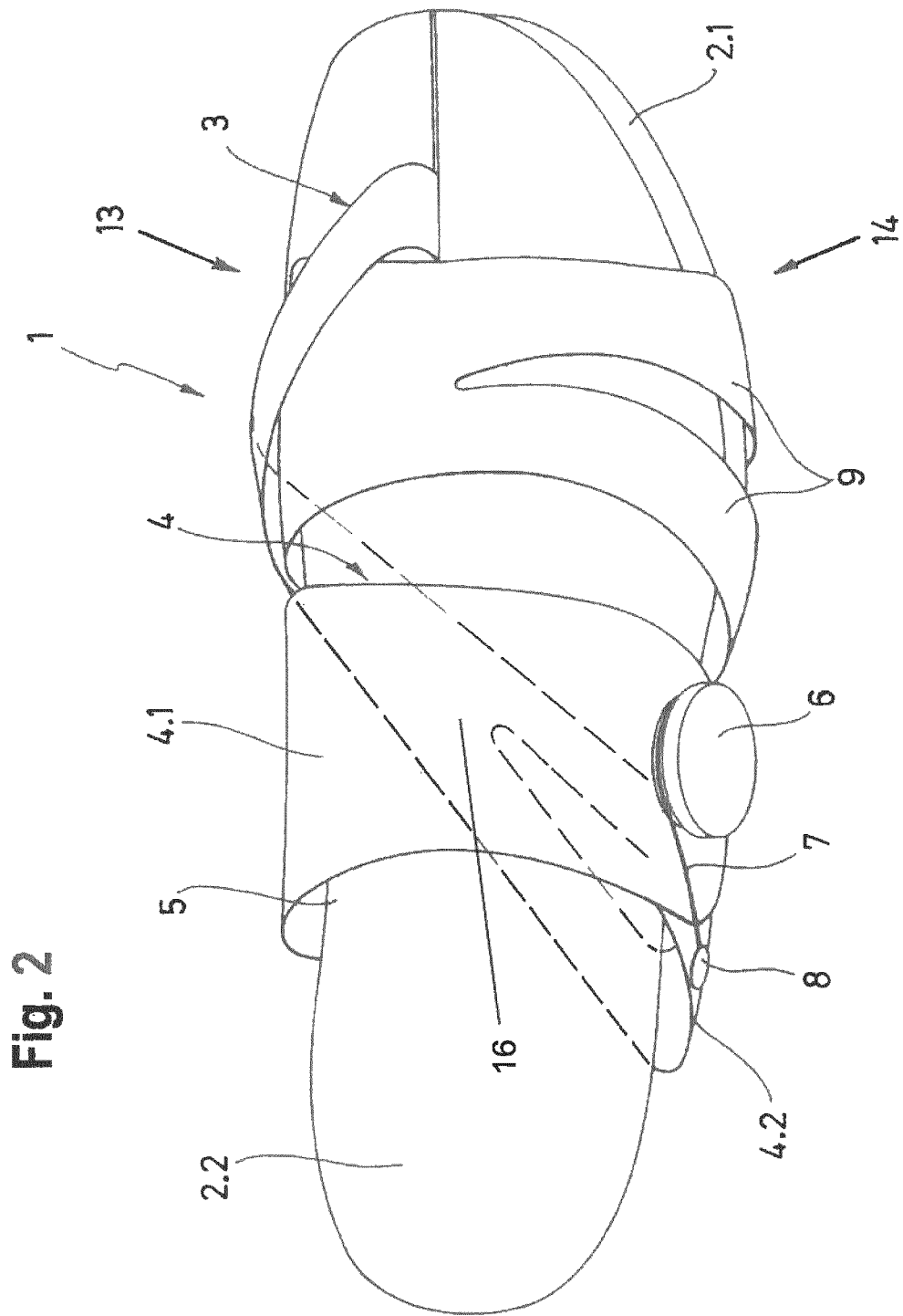
FIG. 2 shows a perspective view as a top view of the sandal depicted in FIG. 1.

In FIG. 2, a perspective top view of the sandal depicted in FIG. 1 is shown, wherein dashed lines schematically represent the integrated coupling of the metatarsus strap section 4 with the great toe strap section 3 underneath the footbed 2.2, i.e. between the bottom side of the footbed and the actual outsole 2.1. These dashed lines also indicate the position and shape of the channel 16, which extends in the metatarsus region from the foot inner side to the foot outer side. The foot outer side part 4.2 passes through the sandal via the channel 16 underneath the footbed 2.2, comes out at the foot inner side and forms the strap of the great toe strap section 3. The rotary knob 6 is provided at the foot inner side part 4.1 of the metatarsus strap section 4. Tension elements 7 in the form of ropes are provided and fixed to the attachments 8 arranged at the foot outer side part 4.2 of the metatarsus strap section 4 such that, upon rotating the rotary knob 6, the tension elements 7 are wound up or unwound, thereby decreasing or, if the rotary knob is rotated counterclockwise, increasing the wrap length of the metatarsus strap section 4. In this way, the pressure acting on the metatarsal bone and thus the corrective force and, accordingly, the therapeutic effect is adjustable. The foot inner side part 4.1 overlaps the raised edge 5 of the footbed 2.2 such that, upon decreasing the wrap length of the metatarsus strap section 4, the corrective force exerted on the metatarsal bones and facing the foot inner side is increased. At the same time, due to the coupling of the metatarsus strap section 4 with the great toe strap section 3, the great toe strap section is tightened upon decreasing the wrap length such that a corresponding corrective force is exerted on the great toe. The remaining basic design corresponds to view described in FIG. 1. The foot outer side part 4.2 of the metatarsus strap section 4, which in fact provides the coupling to the great toe strap section 3, has an end region which faces the foot inner side part which consists of two ends which, in the course of the coupling and via a recessed tongue, are merged into an undivided part again. This region of the coupling is arranged adjacent to the great toe strap in front of its exit underneath the footbed 2.2

Figure 3:
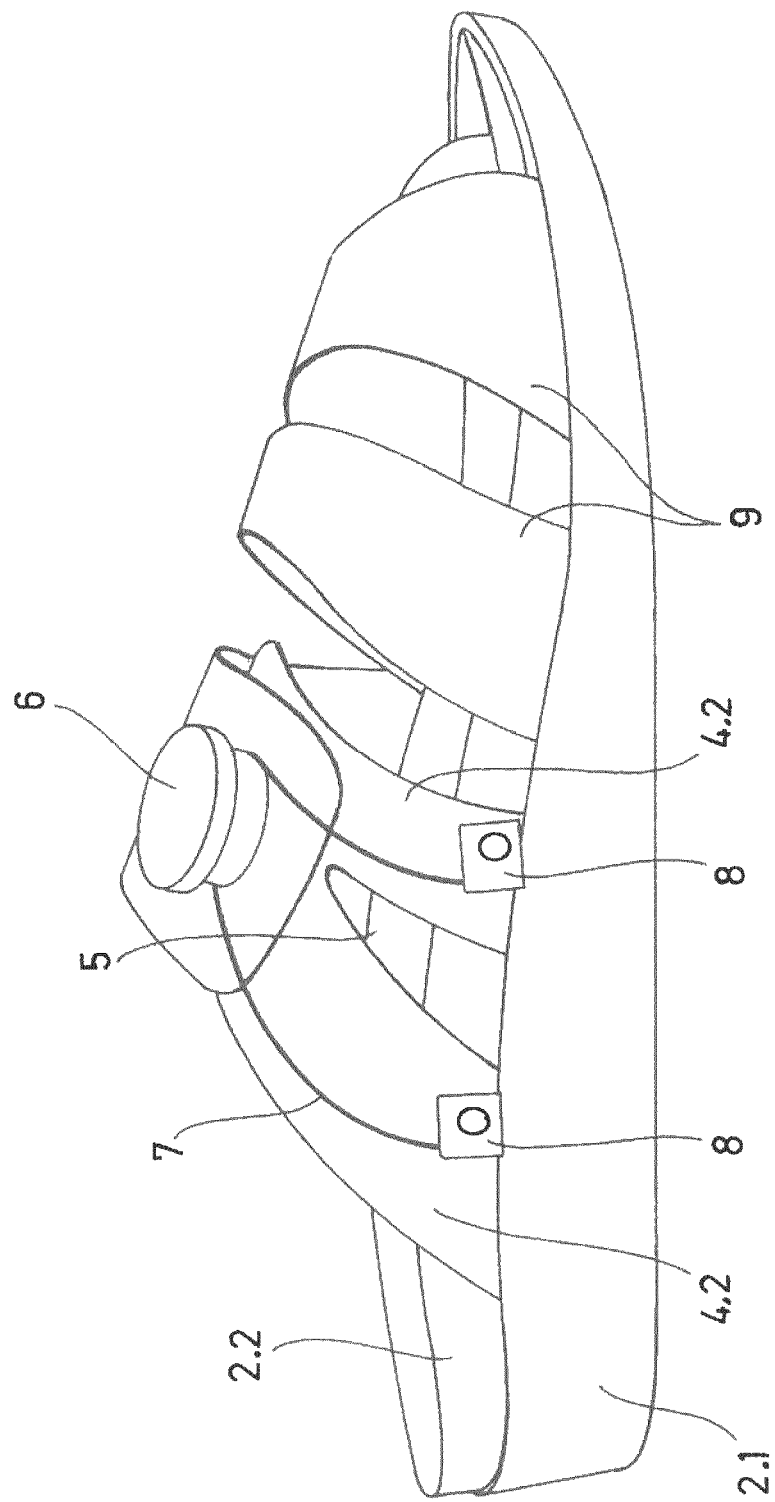
FIG. 3 shows a perspective view as a side view of the foot outer side of the sandal according to the disclosure.

In FIG. 3, a perspective side view of the embodiment depicted in FIG. 1 or FIG. 2 is shown. On the one hand, it is illustrated that the footbed 2.2 is inserted in the sandal in the form of an insole. On the other hand, the foot outer side part of the metatarsus strap section 4 is illustrated such that it consists of two connecting links or lugs, at each of which one an attachment 8 is provided. The tension elements 7 are guided by the attachments 8 towards the rotary knob 6 such that, upon rotating the rotary knob, the rope can be shortened or lengthened, thereby causing shortening or lengthening of the wrap length of the metatarsus strap section 4. In this way, a corresponding therapeutic effect is adjustable. Upon decreasing the wrap length, the corrective force increases which is exerted to the metatarsal bones on the foot inner side, whereas this force decreases upon increasing the wrap length. As a result, the patient is enabled to eventually decide about the therapeutic effect to some extent by adapting the tightness of the strap section in dependence on the desired therapeutic success. In the view depicted in FIG. 3, the intermediate strap sections 9, which are arranged in between the metatarsus strap section 4 and the great toe strap section 3, cover the great toe strap section 3 such that this section is not visible in the Figure.

Figure 4:
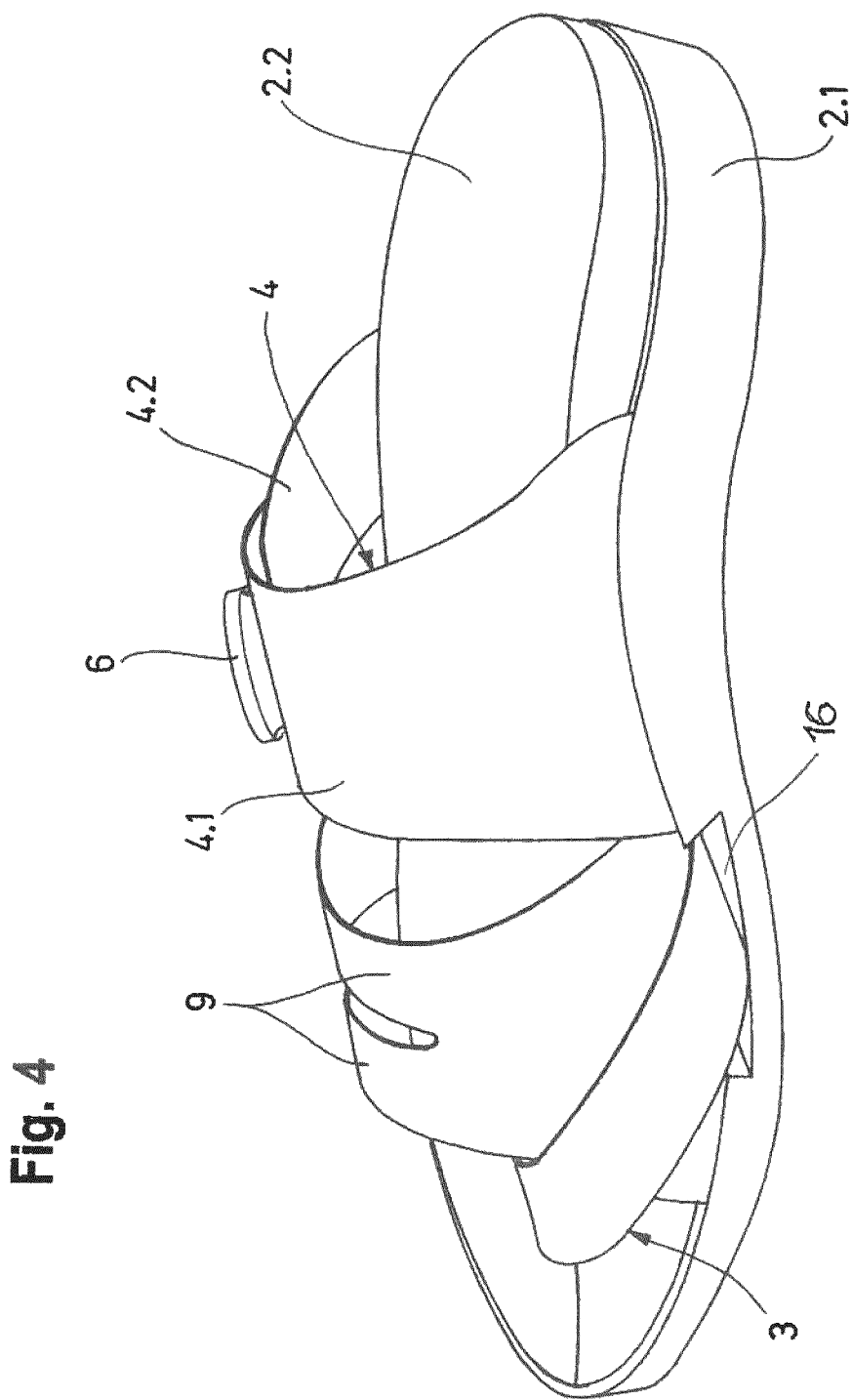
FIG. 4 shows a perspective view from an oblique angle from above in direction of the foot inner side of the sandal according to the disclosure.

In FIG. 4 a perspective side view of the foot inner side is shown which illustrates how the great toe strap section 3 enters the channel 16 in the region of the outsole 2.1 underneath the footbed 2.2 provided in the form of an insole. This great toe section is directly connected to the foot outer side part 4.2 of the metatarsus strap section 4 by means of the coupling such that rotating of the rotary knob 6 causes a variation of the wrap length around the metatarsus region and, at the same time, a tightening of the metatarsus strap section and the great toe strap section 3 if the wrap length is decreased. Accordingly, the tightening may be decreased upon increasing the wrap length. Apart from that, the configuration depicted in FIG. 4 corresponds to the embodiment depicted in FIG. 1.

Figure 5:
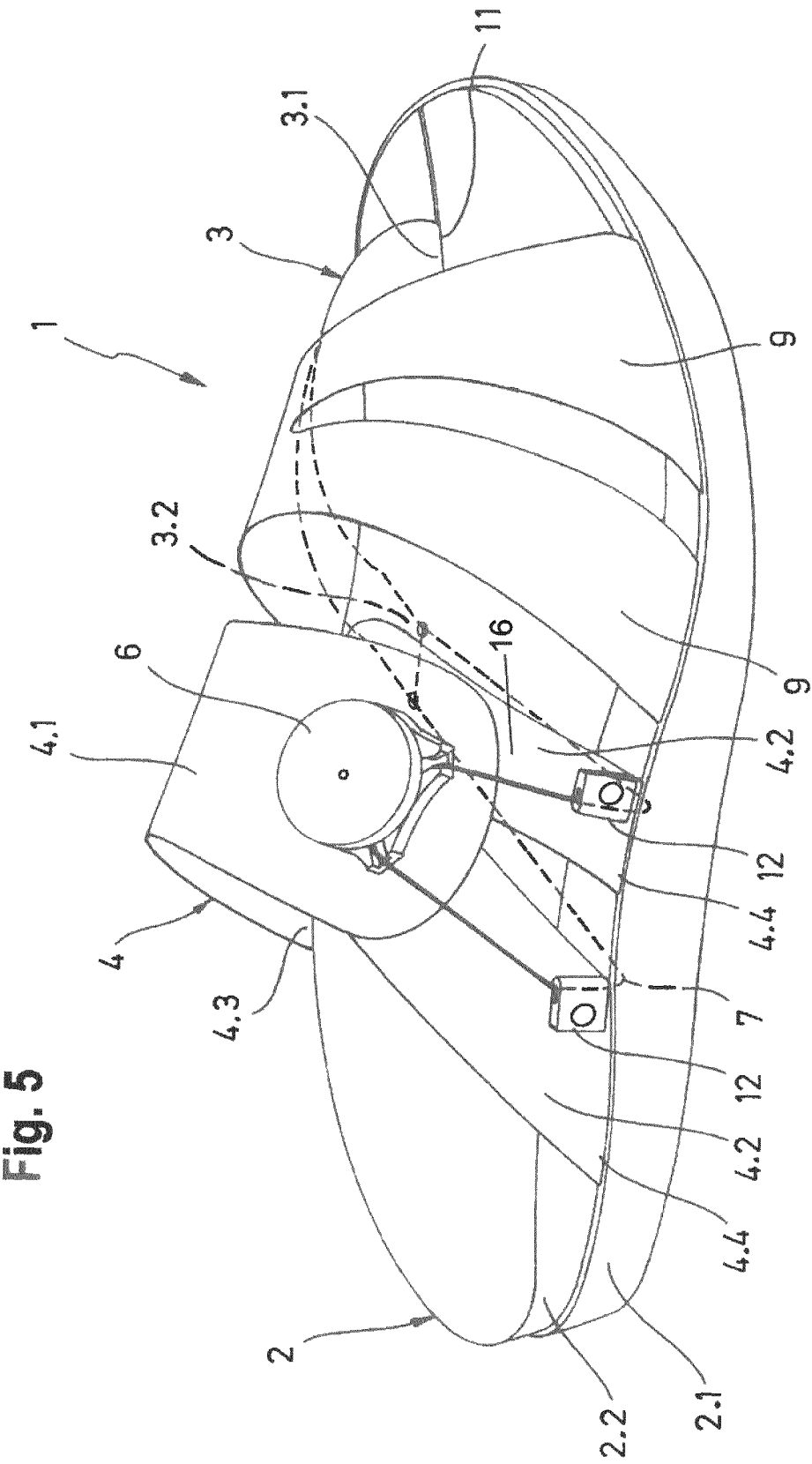
FIG. 5 shows a perspective view from an oblique angle from above in direction of a foot outer side of a sandal according to a second embodiment.

In FIG. 5, a perspective view of a second embodiment is shown from an oblique angle from above in direction of the outer side of the sandal, i.e. that side of the sandal at which the foot outer side 14 is located. Also this hallux valgus sandal comprises a sole element 2 with an actual outsole 2.1 and a footbed 2.2. The footbed may be firmly fixed to the outsole 2.1. However, it is also possible that the footbed 2.2 may be inserted into the outsole 2.1 in the manner of an insole. For assembly reasons, it is also possible that the footbed 2.2 in the form of an insole is inserted into the actual outsole 2.1 and is glued or otherwise firmly fixed thereto. The sandal comprises a divided metatarsus strap section 4 having a foot inner side part 4.1 and a foot outer side part 4.2. The foot outer side part is slotted and comprises two tongue-shaped ends which, likewise to the non-slotted part of the foot outer side part 4.2 of the metatarsus strap section 4, are attached to the sandal between the footbed 2.2 and the actual outsole 2.1. At the foot inner side part 4.1 of the metatarsus strap section 4, the end region 4.3 of which is attached to the sole element 2, a tensioning unit in the form of a rotary knob 6 is provided. A tension element, e.g. a cable, rope or yarn, can be wind onto or unwind from the rotary knob 6. Two such tension elements are provided which are tangentially guided from each side of the rotary knob 6 towards a winding unit underneath the rotary knob 6. The outer foot side part 4.2 of the metatarsus strap section 4, at its end region 4.4, is attached to the sole element 2.

In the region of the connection point between the footbed 2.2 and the actual outsole 2.1 of the sole element 2, one deflection unit 12 is arranged on each tongue-like lug of the foot outer side part 4.2 of the metatarsus strap section 4, from which the respectively deflected tension element or cable is directed into the channel 16 within the sandal 1. In the channel 16, the position of which in the sole region is illustrated in FIG. 5 by dashed lines, the respective end of the tension element 7 is connected to the second end region 3.2 of the great toe strap section 3. The great toe strap section 3 is guided from its fixation 11 around the great toe 10 up to its entry into the inside of the sandal 1 at the foot inner side or at the side of the sandal which faces the inner side of the foot. At this side, the two ends of the tension element 7 are deflected. This means that the second end region 3.2 of the great toe strap section 3 is guided via the ropes and the deflection units 12 to the rotary knob 6 at the foot inner side part 4.1 of the metatarsus strap section 4. Upon rotating the rotary knob 6, the respective tension element is wound up or unwound such that, for example, the tensile stress generated upon winding up not only increases the degree of overlapping between the foot inner side part 4.1 and the foot outer side part 4.2 of the metatarsus strap section 4, but also decreases the wrap length of the metatarsus strap section 4 due to the increase of overlap. As a result, the great toe strap section 3 is tightened, thereby increasing the corrective force acting on the great toe 10.

According to a not shown embodiment, the coupling between the metatarsus strap section 4 and the great toe strap section 3 as depicted in FIGS. 1 to 5 or as provided by an additional tension element as depicted in FIG. 5 is not provided. Rather, each one of the metatarsus strap section 4 and the great toe strap section 3 comprises its own tensioning unit preferably in the form of a rotary knob 6 such that, in this not shown embodiment, adjustment of the corrective force is individually performed either in the great toe range or in the metatarsus range or in both.

In FIG. 6, a view of a foot on the front of the sole element 2 is shown, wherein for a simplified representation, the strap sections are omitted. The great toe 10 is positioned on a wedge-shaped elevation which extends in a foot inner side direction towards the toe and which additionally supports the toe when being circularly enclosed by the great toe strap section 3. When the wrap length of the great toe strap section 3 is decreased and thus the corrective force applied to the great toe increases, the wedge-shaped elevation 15 prevents or counteracts a rotation of the great toe around its longitudinal axis during the therapeutic treatment upon applying the corrective force by means of the great toe strap section 3. Thus, the wedge-shaped elevation 15 serves as a support or a lateral support of the great toe 10 and is inclined transvers to a longitudinal direction of the foot, i.e. the wedge-shaped elevation 15 rises in the medial direction and descends in the lateral direction. The wedge-shaped elevation 15 may be a part of the footbed 2.2 of the sole element 2 or may be attached to the upper side thereof by means of an appropriate coupling, in particular adhesive coupling.

FIG. 7 is a perspective view in the form of a side view of the foot inner side of the sandal according to a further embodiment. The sandal 1 comprises an outsole 2.1 on which a footbed 2.2 is arranged. On the footbed 2.2 a banding 17 is provided in the metatarsus region which extends across the sandal 1. The banding 17 is built up from a plurality of bands 18, wherein a part of the bands 18 is firmly fixed to the footbed 2.2. The great toe strap section 3, at its first end region 3.2, is fixed to the footbed 2.2 and guided obliquely backwards to the channel 16. In this region, the great toe strap section 3 enters into the inside of the footbed 2.2 via the channel 16, where it merges with the metatarsus strap section 4 so as to, together with the metatarsus strap section 4, come out at the outer side of the footbed 2.2 or to be coupled to a tension element 7, as depicted in FIG. 8. The tensioning of the great toe strap section 3 and the metatarsus strap section 4 is performed via the tension elements 7 as described above which can be tightened or untightened by means of the rotary knob 6.

FIG. 8 depicts a perspective top view of the sandal 1 depicted in FIG. 7.

FIG. 9 shows a further embodiment of the sandal, the basic design of which corresponds to that one depicted in FIG. 7 or FIG. 8. However, the metatarsus strap section 4 is not designed in the form of a banding, but comprises two wide flaps which can overlap and which can be adjusted in their desired strap size by means of a Velcro fastener. The sandal also comprises a footbed 2.2 on which an intermediate strap section 9 in the metatarsus region near the metatarsus strap section 4 in the described configuration is arranged, wherein the metatarsus strap section 4 has an foot inner side part 4.1 and a foot outer side part 4.2 which can be adjusted relative to one another by means of a rotary knob 6 and a tension element 7, and wherein the great toe strap section 3 is attached to the footbed 2.2 with a first end region 3.1 and is guided obliquely backwards to the channel 16 which is not shown in FIG. 9. At this position, it enters into the footbed 2.2, where it is merged with the metatarsus strap section 4 or the foot outer side part 4.2 so as to, together therewith, come out from the other side of the footbed 2.2. However, it is also possible that the great toe strap section 3 may be coupled to one tension element, respectively, as depicted in FIG. 8. The tensioning of the great toe strap section 3 and the metatarsus strap section 4 is performed via the tension elements 7 as described above which can be tightened or untightened by means of the rotary knob 6.

In the region between the metatarsus strap section 4 and the great tow strap section 3, an intermediate strap section 9 is provided which is provided in the form of a flap band having a Velcro fastener. The flap band acts as the banding 17 as depicted in FIGS. 7 and 8 having a plurality of bands which are cumulated and constitute the flap band.

LIST OF REFERENCE NUMERALS

1 hallux valgus sandal
2 sole element
2.1 outsole
2.2 footbed
3 great toe strap section
3.1 first end region
3.2 second end region
4 metatarsus strap section
4.1 foot inner side part
4.2 foot outer side part
4.3 end region of the foot inner side part
4.4 end region of the foot outer side part
5 raised edge
6 rotary knob
7 tension element
8 attachment
9 intermediate strap section
10 great toe
11 fixation
12 deflection unit
13 foot inner side
14 foot outer side
15 wedged-shape elevation
16 channel
17 banding
18 firm bands

The invention claimed is:

1. A hallux valgus sandal for treating malpositions of at least great toes and metatarsal bones, comprising:
    a sole element having an outsole and a footbed configured to be attached to a foot when being worn at the foot,
    a metatarsus strap section fixed to the sole element and configured for holding the sandal at the foot, and
    a great toe strap section
    comprising a first end region which is fixed to or embedded in the sole element in a region of the sole element arranged to be between the great toe and an adjacent toe and configured to be variably adjustable in a wrap length around the great toe such that the great toe strap section exerts an adjustable corrective force on the great toe,
    the great toe strap section being guided obliquely backwards from the first end region over the region of the great toe and, at an inner side of the hallux valgus sandal, entering a channel in the sole element which leads to an outside of the hallux valgus sandal,
    wherein
    the metatarsus strap section comprises a foot inner side part and a foot outer side part wherein the foot inner side part of the metatarsus strap section is coupled to the great toe strap section, and
    the channel is configured to be arranged behind a metatarsophalangeal joint of the foot in the metatarsus region of the hallux valgus sandal such that the great toe strap section covers the metatarsus strap section at an entry region into the outsole.

2. The hallux valgus sandal of claim 1, wherein the metatarsus strap section, at its respective end regions, is fixed to or in the sole element and the wrap length around the metatarsus region is configured to be variably adjustable such that the metatarsus strap exerts an adjustable corrective force on the metatarsus region.

3. The hallux valgus sandal of claim 2 further comprising:
    the great toe strap section configured to laterally fix the position of the great toe, and the metatarsus strap section which is configured to circularly enclose the metatarsal bones of a foot hold on the sole element when the sandal is worn and which is adjustable in its wrap length, wherein
    the metatarsus strap section and the great toe strap section are coupled to one another such that, upon adjusting the wrap length of the metatarsus strap section, an adjustable metatarsal corrective force acts laterally upon the metatarsal bones to press a foot inner side metatarsal bone in a lateral direction towards the outer side of the foot and which, when the metatarsus strap section and the great toe strap section arranged in or on the outsole are coupled, the great toe strap section is simultaneously tightened and is configured to exert a great toe correction force in direction of the inner side of the foot.

4. The hallux valgus sandal of claim 2, wherein the wrap length is decreasable upon pulling the foot inner side part of the metatarsus strap section among its foot outer side part.

5. The hallux valgus sandal of claim 2, wherein the wrap length is decreasable upon folding the metatarsus strap section and increasable upon unfolding the metatarsus strap section.

6. The hallux valgus sandal of claim 2, wherein the footbed at a side facing the inner side of the foot, has a raised edge in the region of the metatarsus strap section which, is configured to exert the corrective force on the metatarsal bone in the manner of a pressure pad when decreasing the wrap length of the metatarsus strap section.

7. The hallux valgus sandal of claim 2, wherein the metatarsus strap section comprises a pad in the region of its foot inner side provided in the form of a pressure pad configured to exert the corrective force on the metatarsal bone upon decreasing the wrap length of the metatarsus strap section.

8. The hallux valgus sandal of claim 4, wherein the variation of the wrap length is effected by means of a tensioning unit provided in the form of a rotary knob and a tension element interacting with the rotary knob, wherein one end of the tension element is attached to the rotary knob on the foot inner side part of the metatarsus strap section and its other end is fixed to a second end region of the great toe strap section on or in the sole element, and wherein the great toe strap section is fixed to the sole element at its opposing first end region.

9. The hallux valgus sandal according to claim 1, wherein the wrap length of the respective strap section is adjustable by means of a tensioning unit provided in the form of a rotary knob which is connected to a tension element wherein the length of the tension element is adjustable and thus the wrap length is adjustable upon actuation of the tensioning unit.

10. The valgus sandal of claim 1, wherein the holding strap section is the metatarsus strap section comprising a foot inner side part and a foot outer side part.

11. The hallux valgus sandal of claim 2, wherein the wrap length is adjustable upon folding or unfolding the metatarsus strap section.

12. The hallux valgus sandal of claim 2, wherein the coupling of the great toe strap section and the metatarsus strap section is provided by integrally connecting the metatarsus strap section to the great toe strap section the sole element.

13. The hallux valgus sandal of claim 8, wherein the rotary knob has a winding section on which the tension element is windable to be shortened or lengthened, and that the rotary knob is lockable in a respectively set winding position associated to a predefined wrap length.

14. The hallux valgus sandal of claim 1, wherein, in the region between the metatarsus strap section and the great toe strap section, an intermediate strap section is formed in the form of a banding or a flap strap having a hook and loop fastener.

* * * * *